United States Patent [19]

Nagl et al.

[11] 4,302,582
[45] * Nov. 24, 1981

[54] PROCESS FOR THE PREPARATION OF A CONDENSATION PRODUCT FROM PHENOTHIAZINE AND P-NITROSOPHENOL

[75] Inventors: Gert Nagl, Frankfurt am Main; Joachim Ribka, Offenbach-Bürgel; Ulrich Gotsmann; Heinz Dickmanns, both of Frankfurt am Main, all of Fed. Rep. of Germany

[73] Assignee: Cassella Aktiengesellschaft, Frankfurt, Fed. Rep. of Germany

[ * ] Notice: The portion of the term of this patent subsequent to Aug. 19, 1997, has been disclaimed.

[21] Appl. No.: 117,127

[22] Filed: Jan. 31, 1980

Related U.S. Application Data

[63] Continuation-in-part of Ser. No. 955,643, Oct. 30, 1978, Pat. No. 4,218,219.

[30] Foreign Application Priority Data

Oct. 29, 1977 [DE] Fed. Rep. of Germany ....... 2748744
Mar. 5, 1979 [DE] Fed. Rep. of Germany ....... 2908486

[51] Int. Cl.$^3$ ............................................. C07D 513/00
[52] U.S. Cl. .................................................... 544/37
[58] Field of Search ......................................... 544/37

[56] References Cited

U.S. PATENT DOCUMENTS 966,092  8/1910  Herz .................................. 544/37 X
1,128,370  2/1915  Schmidt et al. ................... 544/37 X
1,867,863  7/1932  Muth ................................. 544/37 X

OTHER PUBLICATIONS

Beilsteins Handbuch der Organischen Chemie, vol. 27, 4th Ed., pp. 63, 64, 65, 67-68, (System No. 4198), 1937.
Handbuch der Organischen Chemie, vol. 27, 4th Ed., Erstes Erganzungswerk, p. 226 (System No. 4198), 1938.
Lubs, "The Chemistry of Synthetic Dyes and Pigments", 1955, pp. 321-323.
Dutt., J. Chem. Soc., vol. 125, pp. 802-807, 1924.

*Primary Examiner*—Joseph Paul Brust
*Attorney, Agent, or Firm*—Connolly & Hutz

[57] ABSTRACT

An improved process for preparation of a condensed product of phenothiazine and p-nitrosophenol which contains more than 60% by weight of indophenol S-oxide of the formula

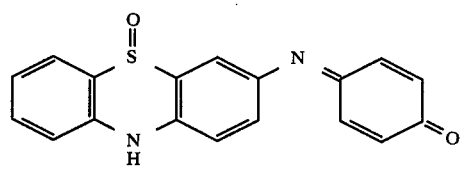

by condensing phenothiazine with p-nitrosophenol in sulphuric acid wherein the improvement comprises the phenothiazine being in 60 to 90% strength sulphuric acid at the time of addition of the p-nitrosophenol.

5 Claims, No Drawings

PROCESS FOR THE PREPARATION OF A CONDENSATION PRODUCT FROM PHENOTHIAZINE AND P-NITROSOPHENOL

This is a continuation-in-part of copending application Ser. No. 955,643 filed Oct. 30, 1978, now U.S. Pat. No. 4,218,219 issued Aug. 19, 1980.

The invention relates to a process for the preparation of a condensation product from phenothiazine and p-nitrosophenol which contains at least 60% by weight of the indophenol S-oxide I

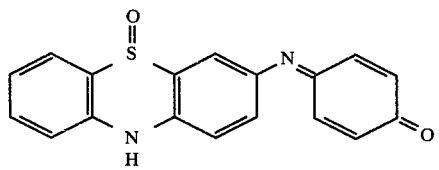

(I)

According to "Journal of the Chemical Society London", Volume 125, pages 802 and 803 (1924), it is possible to subject phenothiazine to a condensation reaction with p-nitrosophenol in concentrated sulphuric acid and to fuse the resulting condensation product with sulphur and sodium sulphide at 250° to 300° to give green sulphur dyestuffs. However, the sulphur dyestuffs prepared in this manner have a number of serious disadvantages, in particular poor yield, low tinctorial strength, contamination by starting materials and by-products, incomplete solubility in alkali metal dithionite and alkali metal sulphide vats, dull shades, non-uniform occurrence in the production batches and poor fastness properties, in particular fastness to wet processing and fastness to washing with peroxide, and because of these disadvantages they have hitherto found no application in practice. In order to obtain green sulphur dyeings on cotton, it was thus hitherto necessary either to employ sulphur-containing derivatives of copper phthalocyanine, which cannot be vatted with sodium dithionite and the applicability of which is thus limited, and the preparation of which requires a relatively large amount of technical, which makes their use considerably more expensive, or to fall back on green sulphur dyestuffs, such as, for example, Sulphur Green 2, C.I. No. 53, 571, or Sulphur Green 3, C.I. No. 53 570, but these have poor wet fastness properties, in particular a poor fastness to washing with peroxide, and therefore cannot be used for dyeings with a high level of fastness. There was thus an urgent need for a process which enables industrially valuable sulphur dyestuffs which give fast green dyeings on cotton to be prepared in an technologically simple manner.

According to an earlier proposal (German Patent Application No. P 27 48 744.1), this object can be achieved when those condensation products from phenothiazine and p-nitrosophenol which are obtained by also using an additional oxidising agent and which contain at least 60% by weight of the indophenol S-oxide of the formula

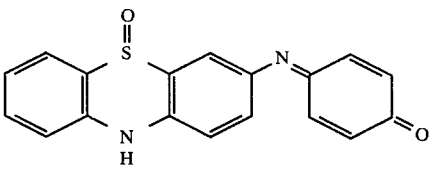

I are subjected to thionation in a bake or reflux process. Additional oxidising agents which can be used in this process are, for example, sulphur trioxide or excess p-nitrosophenol. When p-nitrosophenol is used as the condensation component and as an additional oxidising agent, at least 1.125 mols are employed per mol of phenothiazine. The condensation products from phenothiazine and p-nitrosophenol prepared according to the earlier proposal are obtained in high yields and are virtually free from starting materials and by-products, the presence of which leads to an impairment in the quality of the sulphur dyestuffs prepared from the condensation products. The sulphur dyestuffs have outstanding fastness properties and a valuable shade and can be prepared in high yield, high tinctorial strength and high purity. They are completely soluble in alkali metal dithionite and alkali metal sulphide vats.

It has now been found that condensation products from phenothiazine and p-nitrosophenol which contain at least 60% by weight of the indophenol S-oxide of the formula I and only small amounts of starting materials and by-products can also be obtained by condensation of phenothiazine in sulphuric acid without using an additional oxidising agent if, before the addition of the p-nitrosophenol, the phenothiazine is present in solution in 60 to 90% strength sulphuric acid, preferably in 65 to 88.5% strength sulphuric acid and very particularly preferably in 70 to 86% strength sulphuric acid.

After addition of the p-nitrosophenol to the phenothiazine dissolved in sulphuric acid, the condensation reaction is appropriately carried out at temperatures from −20° to +20° C., preferably from −10° C. to +10° C. The reaction is weakly exothermic, so that the desired reaction temperature must be maintained by cooling. It is advantageous to use a slight excess of p-nitrosophenol. 1.05 to 1.125 mols of p-nitrosophenol are normally employed per mole of phenothiazine. Larger excesses of p-nitrosophenol are not harmful, but are also not necessary. Isolation of the resulting condensation products is effected in the customary manner, for example by introducing the reaction mixture into water and filtering off, washing out, neutralising and drying the product.

The phenothiazine dissolved in sulphuric acid is in the form of the radical cation. The concentration data for the sulphuric acid are given in percentages by weight and, in the context of the present invention, relate only to the amount of the components water and $H_2SO_4$ in the solutions or reaction mixtures. In calculating the sulphuric acid concentration, the consumption of sulphuric acid by the oxidation of the phenothiazine and the salt formation and the formation of water of reaction according to the following equation is also to be taken into consideration.

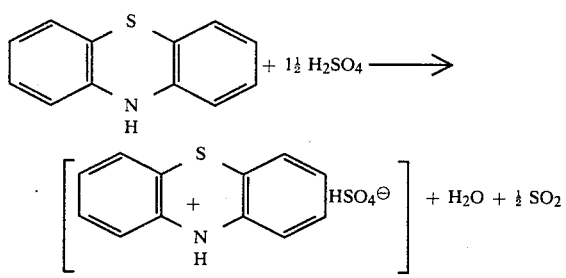

Since phenothiazine dissolves only slowly in dilute sulphuric acid, it is advantageous to first dissolve the phenothiazine in 90 to 100% strength sulphuric acid and to dilute this solution to a sulphuric acid concentration of 60 to 90%, preferably of 65 to 88.5% and very particularly preferably of 70 to 86%, before the condensation reaction with p-nitrosophenol. For carrying out the process according to the invention, 3.5 to 10, preferably 5 to 8, parts by weight of 96% strength to 100% strength sulphuric acid are normally used per one part by weight of phenothiazine. It is not necessary to use more than 10 parts by weight of 96% strength to 100% strength sulphuric acid for dissolving one part by weight of phenothiazine. If the phenothiazine is not dissolved in 96 to 100% strength sulphuric acid but in sulphuric acid which is more dilute, correspondingly more sulphuric acid is required for solution.

The condensation products prepared according to the invention contain phenothiazine and phenothiazine S-oxide together to the extent of less than 6% by weight, and as a general rule even to the extent of less than 4% by weight, and the sum of the chemically undefined by-products is below 20%, and as a general rule even below 10%. The main constituent of the condensation products prepared according to the invention is the indophenol S-oxide of the formula I, in an amount of 60 to 100% by weight, preferably 80 to 100% by weight. The condensation products prepared according to the invention also contain the indophenol of the formula Ia in an amount of 0 to 20% by weight, preferably 0 to 10% by weight.

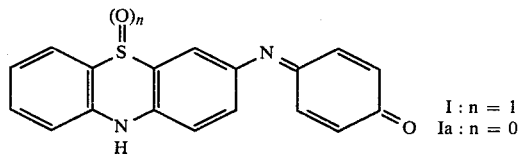

I : n = 1
Ia : n = 0

The compounds of the formulae I and Ia can also be present entirely or partly in their tautomeric forms. The yields of the process according to the invention are good. If the phenothiazine is present in solution in 70 to 86% strength sulphuric acid before the addition of the p-nitrosophenol, a condensation product with a content of the compound I of equal to or greater than 80% by weight is obtained in a yield of about 85% or more of theory. If the phenothiazine is present in solution in 65 to 88.5% strength sulphuric acid, outside the abovementioned range, the condensation product is obtained in about 80% yield and with a percentage content of the compound I of 70 or more. If the phenothiazine is present in solution in 60 to 90% strength sulphuric acid, outside the abovementioned ranges, the condensation product is obtained in a yield of about 75% and with a percentage content of the compound I of 60 or more.

The condensation products prepared according to the invention are outstandingly suitable for the preparation of sulphur dyestuffs. They are converted into sulphur dyestuffs, which give green dyeings on cotton and green to black dyeings on polyamide, by thionating in a bake or reflux process in a manner which is in itself known. These thionation processes are described, for example, in "Venkatarman, The Chemistry of Synthetic Dyes, Volume 2 (1952), page 1062 et seq. and page 1103 et seq. and Volume 7 (1974), page 24 et seq. Academic Press, New York, San Franciso, London". Thionation of the condensation products according to the invention is preferably carried out by the reflux process. Reflux processes which involve the use of alkali metal polysulphide are particularly suitable, 2 to 6 mols, preferably 2.5 to 4 mols, of sodium sulphide and 7 to 30 mols, preferably 13 to 18 mols, of sulphur being employed per mole of the product to be sulphurised. The reflux processes are carried out in the solvents customary for this thionating method. The sulphur dyestuffs which can be obtained from the condensation products prepared by the process according to the invention have outstanding fastness properties and a valuable shade and are obtained in high yield, high tinctorial strength and high purity. They are adequately soluble in alkali metal dithionite and alkali metal sulphide vats,.

In the following embodiment examples, parts are parts by weight; percentage data are given in percent by weight and temperature data are given in degrees Centigrade. Example 1 illustrates the preparation, according to the invention, of the condensation product. Example 2 illustrates, for comparison, the results which are obtained when the condensation reaction is not carried out by the process according to the invention. Examples 3 and 5 illustrate the preparation of sulphur dyestuffs, starting from condensation products prepared according to the invention.

EXAMPLE 1

40 parts of phenothiazine are dissolved in 250 parts of concentrated (96% strength by weight) sulphuric acid at room temperature, whilst cooling. The solution is cooled to 0° C. and 36 parts of ice are added, whilst cooling and stirring vigorously. Taking into consideration the sulphuric acid consumption by oxidation of the phenothiazine and the salt formation and the formation of water of reaction, the calculated concentration of sulphuric acid after adding the ice is 80.94%. The solution is then cooled to −5° C. and 30.5 parts of water-containing 85% strength p-nitrosophenol paste are added, whilst cooling and stirring vigorously. The reaction mixture is subsequently stirred for 4 hours at 0° C., whilst cooling. It is then poured into a vigorously stirring mixture of 1,000 parts of water and 700 parts of ice. The product is filtered off, washed with about 500 parts of water and suspended in water, the suspension is neutralised with sodium hydroxide solution and the product is filtered off, washed until free from salt, dried and ground. About 61 parts of a condensation product with a content of about 88% by weight of the compound of the formula I, about 3% by weight of the compound of the formula Ia, about 2.5% by weight of phenothiazine and about 0.5% by weight of phenothiazine 5-oxide (determination of the content by HPLC) are obtained. Yield of the compound of the formulae I and Ia: about 87% of theory.

EXAMPLE 2

(Comparison example)

40 parts of phenothiazine are dissolved in 250 parts of concentrated (96% strength by weight) sulphuric acid at room temperature, whilst cooling. Taking into consideration the consumption of sulphuric acid by oxidation of the phenothiazine and the salt formation and the formation of water of reaction, the calculated concentration of the sulphuric acid is 93.93%. The solution is cooled to −5° C. and 30.5 parts of water-containing 85% strength p-nitrosophenol paste are added, whilst cooling and stirring vigorously. The reaction mixture is subsequently stirred for 4 hours at 0° C., whilst cooling. It is then poured into a vigorously stirred mixture of 1,000 parts of water and 700 parts of ice. The product is filtered off, washed with about 500 parts of water and suspended in water, the suspension is neutralised with sodium hydroxide solution and the product is filtered off, washed until free from salts, dried and ground. About 59 parts of a condensation product with a content of about 20% by weight of the compound of the formula I, about 30% by weight of the compound of the formula Ia, about 1% by weight of phenothiazine and about 12% by weight of phenothiazine 5-oxide (determination of the content by HPLC) are obtained. The remainder consists of undefined organic compounds.

Yield of the compounds of the formulae I and Ia: about 50% of theory.

EXAMPLE 3

44 parts of the condensation product of Example 1 are introduced into a polysulphide solution of about 70° C., which has been prepared from 205 parts of 95% strength n-butanol, 49 parts of sodium sulphide (60% pure) in the form of flakes and 58 parts of sulphur. The mixture is heated to the boiling point and maintained under reflux for 72 hours, whilst vigorously boiling and stirring. 2.5 parts of sodium nitrite and 25 parts of 95% strength n-butanol are added, without cooling the mixture, and the mixture is stirred under reflux for a further two hours. 300 parts of brine of 24° Bé strength are then added and the butanol is distilled off with steam. The dyestuff is filtered off and washed with brine of 12° Bé strength until free from polysulphide. The filter cake is suspended in hot water and the suspension is adjusted to pH=2 with hydrochloric acid and subsequently stirred at 60° C. for one hour. The product is then filtered off, washed until neutral, dried and ground. About 61 parts of dyestuff are obtained in powder form. The dyestuff dyes cellulose fibres, from alkali metal sulphide solution or alkaline dithionite solution, in green shades of very good fastness to wet processing and light, and dyes polyamide in green to deep black shades of very good fastness to wet processing and light.

The dyestuff is virtually completely soluble in dithionite vats, sulphide vats and bisulphide vats.

EXAMPLE 4

(Comparison example)

If 44 parts of the condensation product from Example 2 are used in Example 3 instead of the condensation product of Example 1, and the procedure followed its otherwise according to the statements of Example 3, about 60 parts of dyestuff are obtained in powder form. The dyestuff differs from the dyestuff from Example 3 by a significantly lower tinctorial strength, a considerably duller and bluer shade and an incomplete solubility in dithionite vats, sulphide vats and hydrogen sulfide vats.

EXAMPLE 5

44 parts of the condensation product of Example 1 are introduced into a polysulphide solution of about 70° C., which has been prepared from 50 parts of water, 50 parts of diethylene glycol monoethyl ether, 30 parts of the sodium salt of m-xylenesulphonic acid, 49 parts of sodium sulphide (60% pure) in the form of flakes and 58 parts of sulphur. The mixture is heated to the boiling point and kept under reflux for 72 hours, whilst vigorously boiling and stirring. The thionation mass is then dissolved by adding 42 parts of the sodium salt of m-xylenesulphonic acid, 53 parts of sodium sulphide in the form of flakes, 160 parts of 30% strength sodium hydrogen sulfide solution and 250 parts of water. A clear, stable solution of the reduced sulphur dyestuff which is water-thin and does not settle out is obtained. Using this ready-to-use dyestuff solution and without addition of reducing agents, green dyeings of very good fastness to wet processing and light are obtained on cellulose fibres and green to deep black dyeings of good fastness to wet processing and light are obtained on polyamide fibres. In this form, the dyestuff is particularly suitable for use in continuously operating dyeing processes.

EXAMPLE 6

(Comparison example)

If 44 parts of the condensation product of Example 2 are used in Example 5 instead of the condensation product of Example 1 and the procedure is otherwise according to the statements of Example 5, a dyestuff which differs from the dyestuff of Example 5 by a significantly lower tinctorial strength, a considerably duller and bluer shade and a tendency to settle out is obtained.

We claim:

1. In the process for preparation of a condensation product of phenothiazine and p-nitrosophenol which contains more than 60% by weight of indophenol-S-oxide of the formula

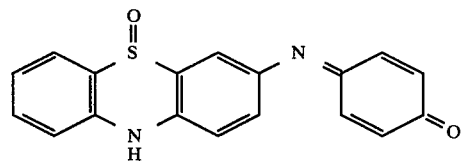

by condensing phenothiazine with p-nitrosophenol in sulphuric acid wherein the improvement comprises the phenothiazine being in 60 to 90% strength sulphuric acid at the time of the addition of p-nitrosophenol in an amount of no more than 1.125 moles per mole of phenothiazine.

2. The process according to claim 1 wherein phenothiazine is present in solution in 65 to 88.5% strength sulphuric acid before the addition of the p-nitrosophenol.

3. The process according to claim 2 wherein phenothiazine is present in solution in 70 to 86% strength sulphuric acid before the addition of the p-nitrosophenol.

4. The process according to claim 1 wherein phenothiazine is first dissolved in 90 to 100% strength sulphuric acid and this solution is then diluted prior to addition of p-nitrosophenol.

5. The process according to claim 1 wherein the amount of p-nitrosophenol is 1.05 to 1.125 moles per mole of phenothiazine.

* * * * *

UNITED STATES PATENT OFFICE
CERTIFICATE OF CORRECTION

Patent No. 4,302,582　　　　　　　　Dated November 24, 1981

Inventor(s) Gert Nagl et al

It is certified that error appears in the above-identified patent and that said Letters Patent are hereby corrected as shown below:

| Column | Line | CHANGE |
|---|---|---|
| 3 | 10 | change |

"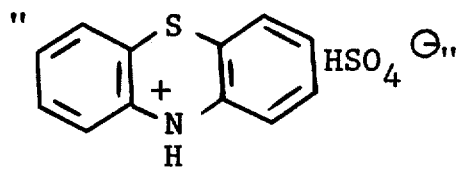"

to

--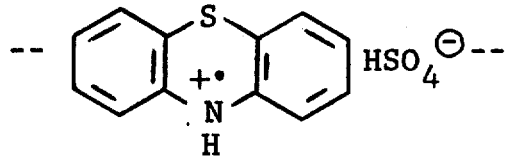--

Signed and Sealed this

Twenty-seventh Day of July 1982

[SEAL]

Attest:

Attesting Officer

GERALD J. MOSSINGHOFF

Commissioner of Patents and Trademarks